United States Patent
Deutscher et al.

(10) Patent No.: US 7,252,433 B2
(45) Date of Patent: Aug. 7, 2007

(54) X-RAY APPARATUS WITH RADIATION SHIELDING THAT ACCEPTS AN UNSHIELDED X-RAY RADIATOR THEREIN

(75) Inventors: Thomas Deutscher, Lauf-Simonshofen (DE); Matthias Seufert, Oberreichenbach (DE); Karin Söldner, Schwaig (DE)

(73) Assignee: Siemens Aktiengesellschaft, Munich (DE)

( * ) Notice: Subject to any disclaimer, the term of this patent is extended or adjusted under 35 U.S.C. 154(b) by 50 days.

(21) Appl. No.: 10/897,697

(22) Filed: Jul. 23, 2004

(65) Prior Publication Data
US 2005/0031085 A1  Feb. 10, 2005

(30) Foreign Application Priority Data
Jul. 25, 2003  (DE)  ................. 103 34 075

(51) Int. Cl.
*H05G 1/02* (2006.01)
(52) U.S. Cl. .......................... 378/203; 378/4
(58) Field of Classification Search ............. 378/193, 378/161, 140, 4, 65, 10, 121, 101–110, 119, 378/203; 250/497.1, 522.1
See application file for complete search history.

(56) References Cited
U.S. PATENT DOCUMENTS

| | | | | |
|---|---|---|---|---|
| 1,275,417 A * | 8/1918 | Gillett | ................. | 378/92 |
| 2,925,499 A * | 2/1960 | Seidel | ................. | 378/104 |
| 4,357,535 A | 11/1982 | Haas | | |
| 4,726,046 A * | 2/1988 | Nunan | ................. | 378/65 |
| 4,737,647 A * | 4/1988 | Stieber | ................. | 250/505.1 |
| 5,528,658 A * | 6/1996 | Hell | ................. | 378/137 |
| 5,604,784 A * | 2/1997 | Widlicka et al. | ................. | 378/203 |
| 5,995,586 A * | 11/1999 | Jahnke | ................. | 378/137 |
| 6,118,852 A * | 9/2000 | Rogers et al. | ................. | 378/140 |
| 6,819,737 B2 * | 11/2004 | Suzuki et al. | ................. | 378/15 |
| 2002/0067631 A1 * | 6/2002 | Lunding et al. | ................. | 363/131 |

FOREIGN PATENT DOCUMENTS

DE  196 39 917  11/1999
WO  WO 0059576 A1 * 10/2000

* cited by examiner

Primary Examiner—Edward J. Glick
Assistant Examiner—John M. Corbett
(74) Attorney, Agent, or Firm—Schiff Hardin LLP

(57) ABSTRACT

An x-ray apparatus that accepts an x-ray radiator therein has shielding for the x-ray leakage radiation originating from the x-ray radiator that is an integral component of (built into) the x-ray apparatus. An x-ray radiator with an x-ray tube and a housing in which the x-ray tube is contained is composed only of materials that are not suitable for absorption of x-rays.

6 Claims, 1 Drawing Sheet

X-RAY APPARATUS WITH RADIATION SHIELDING THAT ACCEPTS AN UNSHIELDED X-RAY RADIATOR THEREIN

BACKGROUND OF THE INVENTION

1. Field of the Invention

The present invention concerns an x-ray apparatus and an x-ray radiator.

2. Description of the Prior Art

A large part of the x-ray radiation produced by the x-ray tube of an x-ray radiator cannot be used for its Intended purpose, to produce an x-ray image of an examination subject or for the purposes of exposure, and is for radiation protection purposes must also be attenuated by means of suitable shielding measures. In order to suitably attenuate the extraneous x-ray radiation, which is know as x-ray leakage radiation, it is conventional for the housing of the x-ray radiator in which the x-ray tube is contained to be provided with a suitable x-ray-absorbing material. For example, the housing of an x-ray radiator is for the most part clad with lead as an x-ray-absorbing material, and is permeable for x-ray radiation only in the region of the x-ray exit window for the useful x-ray radiation.

Such cladding of the housing of the x-ray radiator, however, is relatively expensive. Moreover, the weight of the x-ray radiator, in particular with high-capacity radiators, increases significantly due to the lead cladding.

SUMMARY OF THE INVENTION

An object of the present invention is to provide an x-ray apparatus that allows the weight (mass) of the x-ray radiator used therein to be reduced.

It is a further object of the invention to provide an x-ray radiator having a reduced weight.

The first object in accordance with the invention is achieved by an x-ray apparatus that is adapted to receive an x-ray radiator therein, wherein the shielding for the x-ray leakage radiation originating from the x-ray radiator is an integral component of the x-ray apparatus.

The invention assumes that the x-ray radiator is operated only in connection with the x-ray apparatus. Therefore the overall system, meaning the x-ray apparatus with the x-ray radiator incorporated therein, must satisfy the conditions with regard to the attenuation of the x-ray leakage radiation. In the inventive x-ray apparatus, the shielding for the x-ray leakage radiation originating from the x-ray radiator is an integral component of the x-ray apparatus, meaning the shielding does not need to be a component of the x-ray radiator, but rather is already firmly connected with (i.e., built into) the x-ray apparatus. Consequently, the shielding remains in place given an exchange of the x-ray radiator in the x-ray apparatus and does not need to exchanged (removed) with the x-ray radiator. Suitable material for the shielding is for example lead.

According to an embodiment of the Inventive x-ray apparatus, a suitable location for application of the shielding is the mounting (receptacle) in the x-ray apparatus for receiving the x-ray radiator. In a preferred embodiment of the inventive x-ray apparatus, it is provided that the overall mounting is covered up to the region of an x-ray exit window with material suitable for shielding the x-ray leakage radiation (i.e., radiation absorbing material).

In connection with the present invention, the term x-ray apparatus means any type of x-ray system or device to produce an x-ray image or an x-ray image data set, as well as for therapeutic treatment. In particular, the x-ray apparatus can be an x-ray computed tomography apparatus. In an embodiment of the invention wherein the x-ray apparatus is an x-ray computed tomography apparatus, the shielding is a component of the gantry of the x-ray computed tomography apparatus. In operation of the x-ray computed tomography apparatus, the x-ray radiator is disposed on or in the gantry and rotates together with the gantry around an examination subject.

The second object is achieved in accordance with the invention by an x-ray radiator with an x-ray tube and a housing in which the x-ray tube is contained, wherein the x-ray radiator consists exclusively (only) of materials that are not suitable for absorption of x-rays. Since the x-ray radiator has no shielding for x-ray leakage radiation, it can be more easily and cost-effectively produced.

In a preferred embodiment of the invention, the inventive x-ray radiator is provided for installation in the inventive x-ray apparatus, so that the overall system, from the combination of the inventive x-ray apparatus with the inventive x-ray radiator incorporated therein, fulfills the legal requirements for attenuation of x-ray leakage radiation.

DESCRIPTION OF THE PREFERRED EMBODIMENTS

Figure 1:
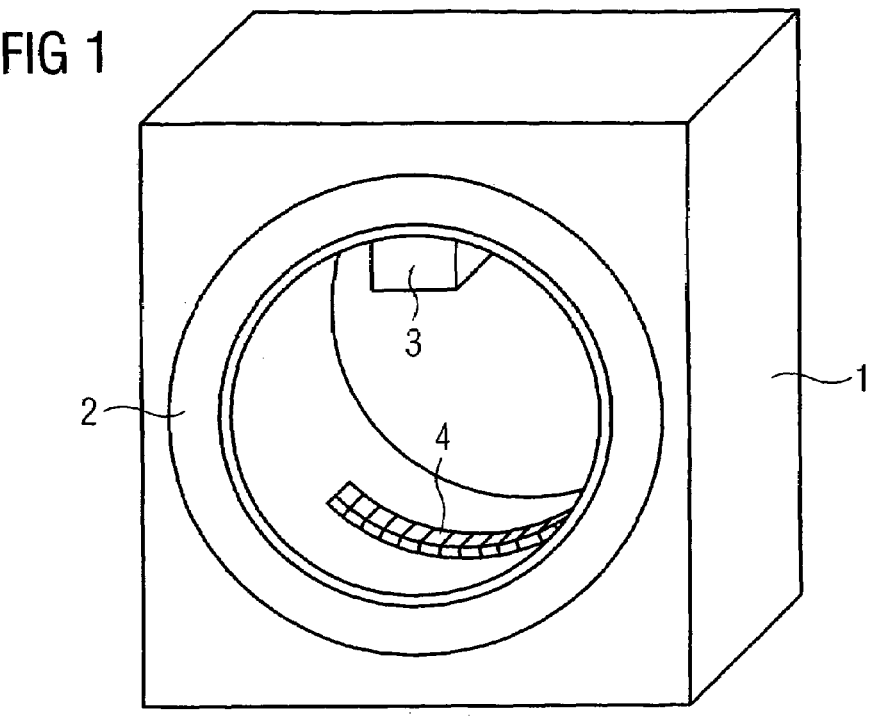
FIG. 1 illustrates an inventive x-ray apparatus.
Figure 2:
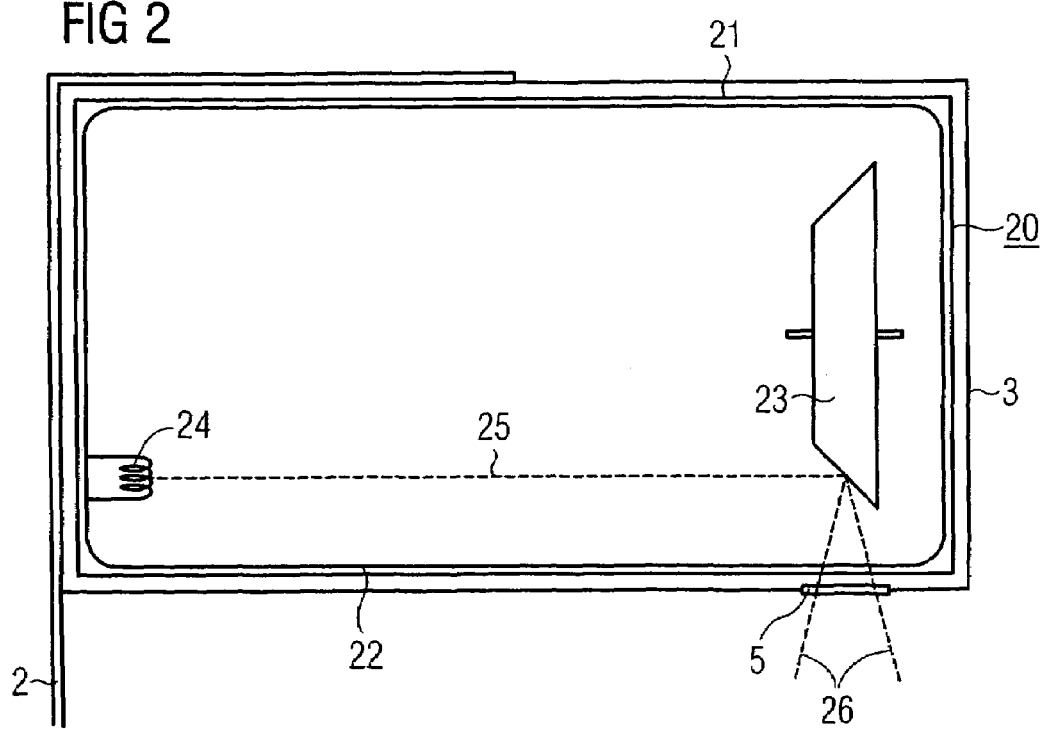
FIG. 2 illustrates the mounting provided for receiving an inventive x-ray radiator in the inventive x-ray apparatus shown in FIG. 1, with the inventive x-ray radiator Incorporated therein.

FIG. 1 shows an x-ray apparatus that, in the exemplary embodiment, is a computed tomography apparatus. The computed tomography apparatus has a stationary housing 1 and a gantry 2 that can be rotated relative to the stationary housing 1. The gantry 2 has a mounting 3 (shown in detail in FIG. 2) in which an x-ray radiator 20 (shown significantly simplified in FIG. 2) can be installed. In FIG. 2, the x-ray radiator 20 is depicted in the installed state.

An x-ray detector 4 is disposed opposite the mounting 3 on the gantry 2. In operation of the computed tomography apparatus, the gantry 2 rotates with the mounting 3 and the installed x-ray radiator 20 around an examination subject (not shown in Figures) in order to produce an exposure of (irradiate) the region of interest of the examination subject.

The x-ray radiator 20 has a housing 21 in which the x-ray tube 22 is contained. In the exemplary embodiment, the x-ray tube 22 is a rotary anode tube, meaning the anode 23 of the x-ray tube 22 is fashioned as a frustrum (truncated cone) and rotates in the operation of the x-ray radiator 20. An electron beam 25 (shown dashed in FIG. 2) originated from the cathode 24 of the x-ray tube 22 and always strikes new or cooled locations of the anode 23, whereby the durability of the x-ray tube 22 is increased. At the locations on which the electron beam 24 strikes, the anode 23 is provided with a material emitting x-rays, such that a useful x-ray beam (shown dashed in FIG. 2) emanates from the anode 23. In order to reduce the weight (mass) of the x-ray radiator 20, the entire housing 21 of the x-ray radiator 20 is produced from aluminum, meaning the entire x-ray radiator 20 is produced from a material that is substantially transparent for x-rays. In general the housing 21 is produced from a material that does not significantly absorb X-rays.

In the exemplary embodiment the mounting 3 (provided to receive or accept an x-ray radiator, and in particular to accept the x-ray radiator 20 shown in FIG. 2) of the computed tomography apparatus is entirely made of or lined with lead, i.e., it is formed of a material that absorbs x-rays. Thus, in the installed state, x-ray leakage radiation (generated by the x-ray radiator 20 and not shown in the figures) is at least attenuated, if not completely absorbed. Only in the region in which the useful x-ray radiation 26 of the x-ray radiator 20 propagates in the installed state does the mounting 3 have an x-ray exit window 5. In the exemplary embodiment the window 5 is made from aluminum, i.e., a material essentially transparent for x-ray radiation.

Although modifications and changes may be suggested by those skilled in the art, it is the intention of the inventors to embody within the patent warranted hereon all changes and modifications as reasonably and properly come within the scope of their contribution to the art.

We claim:

1. An x-ray computed tomography apparatus comprising:
   a computed tomography scanner having an opening therein adapted to receive an examination subject;
   a gantry rotatably mounted in said scanner for rotation around said opening;
   an unshielded x-ray radiator mounted at said gantry, said unshielded x-ray radiator comprising a cathode and an anode contained in a tube, and a radiator housing containing said tube, said radiator housing being comprised of material that is non-shielding for x-rays, said unshielded x-ray radiator emitting diagnostic x-ray radiation and x-ray leakage radiation by operation of said cathode and said anode in said tube in said radiator housing;
   shielding for said x-ray leakage radiation built into said gantry and conforming at least in part to said radiator housing of said unshielded x-ray radiator to shield against emergence beyond said shielding of said x-ray leakage radiation emitted by said unshielded x-ray radiator, said unshielded x-ray radiator, said shielding and said gantry all being co-rotatable around said opening; and
   a mounting that mounts said radiator housing in said gantry allowing removal of said x-ray radiator, as a unit, with said shielding remaining built into said gantry.

2. An x-ray apparatus as claimed in claim 1 wherein said mounting is comprised of material for shielding said x-ray leakage radiation and forming at least a part of said built-in shielding.

3. An x-ray apparatus as claimed in claim 2 wherein said mounting comprises an exit window through which said x-ray diagnostic radiation passes, and wherein an entirety of said mounting, except for said x-ray exit window, is comprised of said material.

4. A computed tomography apparatus as claimed in claim 1 wherein said unshielded x-ray radiator is mounted on said gantry.

5. A computed tomography apparatus as claimed in claim 1 wherein said unshielded x-ray radiator is mounted in said gantry.

6. A computed tomography apparatus as claimed in claim 1 wherein said unshielded x-ray radiator has a radiator housing, said radiator housing consisting exclusively of materials that are substantially transparent to said x-ray leakage radiation.

\* \* \* \* \*